US008404633B2

(12) United States Patent
Lozano Soto et al.

(10) Patent No.: US 8,404,633 B2
(45) Date of Patent: Mar. 26, 2013

(54) CD5 PHARMACEUTICAL COMPOSITIONS FOR THE TREATMENT OF INFECTIOUS AND INFLAMMATORY PROCESSES OF FUNGAL ORIGIN

(75) Inventors: Francisco Lozano Soto, Barcelona (ES); Jorge Vera Fernandez, Barcelona (ES)

(73) Assignees: Hospital Clinic I Provincial de Barcelona, Barcelona (ES); Universitat de Barcelona, Barcelona (ES); Fundacio Clinic per a la Recerca Biomedica, Barcelona (ES)

( * ) Notice: Subject to any disclaimer, the term of this patent is extended or adjusted under 35 U.S.C. 154(b) by 0 days.

(21) Appl. No.: 13/000,005

(22) PCT Filed: Jun. 19, 2009

(86) PCT No.: PCT/EP2009/057649
§ 371 (c)(1), (2), (4) Date: Apr. 19, 2011

(87) PCT Pub. No.: WO2009/153336
PCT Pub. Date: Dec. 23, 2009

(65) Prior Publication Data
US 2011/0195894 A1    Aug. 11, 2011

(30) Foreign Application Priority Data
Jun. 20, 2008  (ES) .................................. 200801860

(51) Int. Cl.
*A61K 38/00* (2006.01)
*A61K 31/00* (2006.01)
*A01N 37/00* (2006.01)
*A61P 31/10* (2006.01)

(52) U.S. Cl. ............ 514/1.1; 514/1.4; 514/3.3; 514/3.4; 514/3.5

(58) Field of Classification Search ........................ None
See application file for complete search history.

(56) References Cited

PUBLICATIONS

Iliev et al. (2012, Science 336:1314-1317).*
Pelvic inflammatory disease, www.medicalnewstoday.com/articles/177923.php, accessed Aug. 6, 2012.*
Nosanchuk (2002, Front. Bioscience 7:1423-1438).*
Axtell, et al., "Cutting Edge: Critical Role for CD5 in Experimental Autoimmune Encephalomyelitis: Inhibition of Engagement Reverse Disease in Mice" *J. Immunology* (2004) 173: 2928-2932.
Aruffo et al., The lymphocyte glycoprotein CD6 contains a repeated domain structure characteristic of a new family of cell surface and secreted proteins. J Exp Med 174:949-952 (1991).
Berland et al., Origins and functions of B-1 cells with notes on the role of CD5. Annu Rev Immunol 20:253-300 (2002).
Biancone et al., Identification of a novel inducible cell-surface ligand of CD5 on activated lymphocytes. J Exp Med 184:811-819 (1996).
Bodian et al., Identification of residues in CD6 which are critical for ligand binding. Biochemistry 36:2637-2641 (1997).
Brossard et al., CD5 Inhibits Signaling at the Immunological Synapse Without Impairing Its Formation. J Immunol 170:4623-4629 (2003).
Calvo et al., Human CD5 signaling and constitutive phosphorylation of C-terminal serine residues by casein kinase II. J Immunol 161:6022-6029 (1998).
Calvo et al., Interaction of recombinant and natural soluble CD5 forms with an alternative cell surface ligand. Eur J Immunol 29:2119-2129 (1999).
Calvo et al., Identification of a natural soluble form of human CD5. Tissue Antigens 54:128-137 (1999).
Castro et al., Extracellular isoforms of CD6 generated by alternative splicing regulate targeting of CD6 to the immunological synapse. J Immunol 178:4351-4361 (2007).
Doi et al., Charged collagen structure mediates the recognition of negatively charged macromolecules by macrophage scavenger receptors. J Biol Chem 268:2126-2133 (1993).
Elomaa et al., Structure of the human macrophage MARCO receptor and characterization of its bacteria-binding region. J Biol Chem 273:4530-4538 (1998).
Freeman et al., an ancient, highly conserved family of cysteine-rich protein domains revealed by cloning type I and type II murine macrophage scavenger receptors. Proc Natl Acad Sci U S A 87:8810-8814 (1990).
Genovese et al., Treatment with a novel poly(ADP-ribose) glycohydrolase inhibitor reduces development of septic shock-like syndrome induced by zymosan in mice. Crit Care Med 32:1365-1374 (2004).
Gimferrer et al., the accessory molecules CD5 and CD6 associate on the membrane of lymphoid T cells. J Biol Chem 278:8564-8571 (2003).
Gimferrer et al., Relevance of CD6-mediated interactions in T cell activation and proliferation. J Immunol 173:2262-2270 (2004).
Gordon, S., Pattern recognition receptors: doubling up for the innate immune response. Cell 111:927-930 (2002).
Haas et al., The identification and characterization of a ligand for bovine CD5. J Immunol 166:3158-3166 (2001).
Hassan et al., Frontline: Optimal T cell activation requires the engagement of CD6 and CD166. Eur J Immunol 34:930-940 (2004).
Hassan et al., CD6 regulates T-cell responses through activation-dependent recruitment of the positive regulator SLP-76. Mol Cell Biol 26:6727-6738 (2006).
Hohenester et al., Crystal structure of a scavenger receptor cysteine-rich domain sheds light on an ancient superfamily. Nat Struct Biol 6:228-232 (1999).
Ibanez et al., Mitogen-activated protein kinase pathway activation by the CD6 lymphocyte surface receptor. J Immunol 177:1152-1159 (2006).

(Continued)

*Primary Examiner* — Elizabeth C Kemmerer
(74) *Attorney, Agent, or Firm* — Knobbe Martens Olson & Bear LLP

(57) ABSTRACT

The present invention refers to pharmaceutical compositions comprising the soluble CD5 ectodomain and its use for the prevention and/or treatment of fungal infections and/or fungal sepsis, as well as inflammatory disorders of fungal origin.

7 Claims, 7 Drawing Sheets

PUBLICATIONS

Janeway et al., Innate immune recognition. Annu Rev Immunol 20:197-216 (2002).

Jiang et al., Identification and characterization of murine SCARA5, a novel class A scavenger receptor that is expressed by populations of epithelial cells. J Biol Chem 281:11834-11845 (2006).

Jones et al., Isolation of complementary DNA clones encoding the human lymphocyte glycoprotdn T1/Leu-1. Nature 323:346-349 (1986).

Kohfeldt et al., Properties of the extracellular calcium binding module of the proteoglycan testican. FEBS Lett 414:557-561 (1997).

Kristiansen et al., Identification of the haemoglobin scavenger receptor. Nature 409:198-201 (2001).

Lankester et al., CD5 is associated with the human B cell antigen receptor complex. Eur J Immunol 24:812-816 (1994).

Lecomte et al., Molecular linkage of the mouse CD5 and CD6 genes. Immunogenetics 44:385-390 (1996).

Levitz et al., Phenotypic and functional characterization of human lymphocytes activated by interleukin 2 to directly inhibit growth of Cryptococcus neoformans in vitro J. Clini. Invest. vol. 91:1490-1498 (1993).

Liu et al., The human genome: an immuno-centric view of evolutionary strategies. Trends Immunol 22:227-229 (2001).

Lozano et al., CD5 signal transduction: positive or negative modulation of antigen receptor signaling. Crit Rev Immunol 20:347-358 (2000).

Mota et al., Poly (ADP-ribose) polymerase-1 inhibition increases expression of heat shock proteins and attenuates heat stroke-induced liver injury. Crit Care Med 36:526-534 (2008).

Nischt et al., Recombinant expression and properties of the human calcium-binding extracellular matrix protein BM-40. Eur J Biochem 200:529-536 (1991).

Padilla et al., Genomic organization of the human CD5 gene. Immunogenetics 51:993-1001 (2000).

Peiser et al., Macrophage class A scavenger receptor-mediated phagocytosis of Escherichia coli: role of cell heterogeneity, microbial strain, and culture conditions in vitro. Infect Immun 68:1953-1963 (2000).

Pospisil et al., CD5 is a potential selecting ligand for B cell surface immunoglobulin framework region sequences. J Exp Med 184:1279-1284 (1996).

Raman, C., CD5, An important regulator of lymphocyte selection and immune tolerance. Immunol Res 26:255-263 (2002).

Ramos-Casals et al., High circulating levels of soluble scavenger receptors (sCD5 and sCD6) in patients with primary Sjogren's syndrome. Rheumatology (Oxford) 40:1056-1059 (2001).

Rodamilans et al., Crystal structure of the third extracellular domain of CD5 reveals the fold of a group B scavenger cysteine-rich receptor domain. J Biol Chem 282:12669-12677 (2007).

Santoni et al., Immune cell-mediated protection against vaginal candidiasis: evidence for a major role of vaginal CD4+ T cells and possible participation of other local lymphocyte effectors. Infect. Immun. vol. 70(9), 4791-4797 (2002).

Sarrias et al., The Scavenger Receptor Cysteine-Rich (SRCR) domain: an ancient and highly conserved protein module of the innate immune system. Crit Rev Immunol 24:1-37 (2004).

Sarrias et al., Biochemical characterization of recombinant and circulating human Spalpha. Tissue Antigens 63:335-344 (2004).

Sarrias et al., A role for human Sp alpha as a pattern recognition receptor. J Biol Chem 280:35391-35398 (2005).

Sarrias et al., CD6 binds to pathogen-associated molecular patterns and protects from LPS-induced septic shock. Proc Natl Acad Sci U S A 104:11724-11729 (2007).

Simarro et al., The cytoplasmic domain of CD5 mediates both TCR/CD3-dependent and -independent diacylglycerol production. J Immunol 159:4307-4315 (1997).

Skonier et al., Mutational analysis of the CD6 ligand binding domain. Protein Eng 10:943-947 (1997).

Van de Velde et al., The B-cell surface protein CD72/Lyb-2 is the ligand for CD5. Nature 351:662-665 (1991).

Vera et al., The CD5 ectodomain interacts with conserved fungal cell wall components and protects from zymosan-induced septic shock-like syndrome. PNAS 106(5): 1506-1511 (2009).

Zimmerman et al., Long-term engagement of CD6 and ALCAM is essential for T cell proliferation induced by dendritic cells. Blood 107:3212-3120 (2006).

* cited by examiner

A

B

C

CD5 PHARMACEUTICAL COMPOSITIONS FOR THE TREATMENT OF INFECTIOUS AND INFLAMMATORY PROCESSES OF FUNGAL ORIGIN

RELATED APPLICATIONS

This application is a U.S. National Phase of International Application No. PCT/EP2009/057649, filed Jun. 19, 2009, designating the U.S. and published on Dec. 23, 2009 as WO 2009/153336, which claims priority to Spanish Patent Application No. P200801860, filed Jun. 20, 2008. The content of these applications is incorporated herein by reference in its entirety.

SEQUENCE LISTING

The Sequence Listing in electronic format is provided as a file entitled HERR52001APC.TXT, created Dec. 17, 2010, which is 1,170 bytes in size. The information in the electronic format of the Sequence Listing is incorporated herein by reference in its entirety.

FIELD OF THE INVENTION

The present invention belongs to the field of fungal infections. It specifically refers to pharmaceutical compositions comprising the soluble CD5 ectodomain for the prevention and/or treatment of fungal infections and/or fungal sepsis, as well as inflammatory disorders of fungal origin.

BACKGROUND OF THE INVENTION

Pathogen recognition by the innate immune system relies on a limited number of fixed germline-encoded receptors which have evolved to identify conserved microbial structures both not shared by the host and essential for their survival, the so-called pathogen-associated molecular patterns (PAMPs) (1, 2). Examples of PAMPs are lipopolysaccharide (LPS) from Gram-negative bacteria, lipoteichoic acid (LTA) and peptidoglycan (PGN) from Gram-positive bacteria, lipoarabinomannan from mycobacteria, and β-glucans and mannan from fungi. Several structurally and functionally diverse classes of pattern-recognition receptors (PRRs) exist which induce various host defense pathways. Protein domains involved in pattern recognition include, among others, the C-type lectin domain from Dendritic Cell (DC) lectins, the leucine-rich repeat (LRR) from Toll-like receptors (TLR), and the scavenger receptor cysteine-rich (SRCR) (2). The later was first described upon cloning of mouse type I class A macrophage scavenger receptor (SR-AI) (3). Sequence comparison with several other proteins, such as the sea urchin speract receptor, human and mouse CD5, and complement factor I revealed the existence of a conserved, 100 amino acid-long motif characteristic of a new superfamily of protein receptors, named the SRCR-SF. This family is currently composed of more than 30 different cell-surface and/or secreted proteins with representatives in most animal phyla, from low invertebrates to mammals (4). The members of the SRCR-SF are divided into two groups: group A members contain SRCR domains composed of 6 cysteines and encoded by two exons, whereas those of group B contain 8 cysteines and are encoded by a single exon. Recent structural data indicate, however, that both group A and B SRCR domains share a similar scaffold (a central core formed by two antiparallel β-sheets and one α-helix), the main differences being observed at the connecting loops (5). This situation recalls that of other few successful protein modules of the immune system from which evolution has settled and built a myriad of different proteins (e.g., immunoglobulin domain). The versatility of these conserved domains lies in the fact that key residues stabilizing the domain structure are conserved throughout evolution while other can evolve freely (especially those at the external loops) giving rise to great functional diversity (6). Accordingly, in spite of their high degree of structural and phylogenetic conservation there is not a unifying function reported for the SRCR domains. Some of them have been involved in protein-protein interactions being the most well studied examples of it the interaction of the CD6 lymphocyte receptor with CD166/ALCAM, a transmembrane adhesion molecule belonging to the Ig superfamily (7, 8), and that of the CD163/M130 macrophage receptor with the haemoglobin-haptoglobin complex (9). A few members of both group A (i.e., SR-AI/II, MARCO, and SCARA5) and B (i.e., DMBT1, Spα, and CD6) SRCR-SF are also known to interact with PAMPs present on bacterial surfaces, such as LPS, LTA and PGN. Although these interactions were initially mapped outside the SRCR domain (10), recent evidence demonstrate the direct involvement of SRCR domains on it (11-14). Therefore, whether pathogen scavenging is a general property shared by all members of the SRCR-SF or only by a selected group of its members remains to be analyzed.

The transmembrane type I receptors CD5 and CD6 are two lymphoid group B members of the SRCR-SF. Both share important similarities at structural and functional level and are encoded by contiguous genes in the same chromosome region thought to derive from duplication of a common ancestral gene (15, 16). CD5 and CD6 are expressed on thymocytes from early stages of their development, on mature peripheral T cells, and on B1a cells, a small subset of mature B cells responsible for the production of polyreactive natural antibodies and which is expanded in certain autoimmune diseases and in B-cell chronic lymphocytic leukemias (17). The extracellular regions of both CD5 and CD6 are exclusively composed of three consecutive group B SRCR domains, which show extensive amino acid sequence identity (5). The main differences between CD5 and CD6 are found at their large cytoplasmic regions, both of which are devoid of intrinsic catalytic activity but contain several structural motifs compatible with a function in signal transduction (18, 19). In that regard, CD5 and CD6 are physically associated to the antigen-specific complex present on T (TCR) and B (BCR) cells (20, 21) and co-localize with it at the centre of the immunological synapse (21, 22). Therefore, CD5 and CD6 are well positioned to either positively or negatively modulate the activation and differentiation signals generated by the antigen-specific receptor (22-26) through still incompletely understood and complex signalling pathways (23, 27-29). This is likely achieved through engagement of the CD5 and CD6 ectodomains by different cell surface counter-receptors. While, it is well established that CD6 binds to CD166/ALCAM (30), a bona fide CD5 ligand is still due (31-35). Interestingly, CD5 and CD6 appear to differ at residues critical for binding to CD166/ALCAM (36).

In a previous study, the bacterial binding capabilities of the CD5 and CD6 ectodomains, both known to also exist as soluble forms circulating in serum (37, 38) were explored. The reported data indicated that both soluble and membrane forms of CD6, but not of CD5, bind to the surface of Gram-negative and Gram-positive bacteria through recognition of specific PAMPs (namely, LPS and LTA, respectively) (39).

Other studies have shown that those cells, either T cells or B cells, expressing CD5 receptor in the surface have the capability of recognize and affect, to a greater or lesser extent, the normal development of C. neoformans and C. albicans (48, 49).

However, the mechanism by which this receptor recognizes or has the affinity for fungal cells has not been described nor suggested.

Now, the authors of the present invention have extended these studies to the analysis of the recognition and binding properties of CD5 and CD6 to fungal structures and have shown that, compared to CD6, the CD5 ectodomain is well suited for the recognition of conserved components on fungal cell surfaces, showing for the first time that said extracellular region isolated from the CD5 receptor can provide prophylaxis in vivo itself against an general fungal infection, not only against C. neoformans y C. albicans.

The authors have shown that fungal cells are specifically recognized, bound and aggregated by soluble forms of the CD5 ectodomain. This is done through the recognition of β-glucans, a conserved structural component of fungal cell walls, by the soluble CD5 ectodomain.

Furthermore, the authors of the present invention have surprisingly found that soluble CD5 ectodomains have a protective effect in the mouse model of zymosan-induced septic shock-like syndrome.

These results support the therapeutic utility of the infusion of soluble human CD5 ectodomain for the treatment of septic shock syndrome or other inflammatory processes of fungal origin.

(A) Detection of bound biotin-labelled recombinant soluble CD5 and CD6 proteins (rshCD5-b and rshCD6-b) to commensal (S. pombe) or pathogenic (C. albicans, C. neoformans) fungal cells by Western blot (B) Dose- and $Ca^{2+}$-dependent binding of biotin-labelled rshCD5 to C. albicans (C) Detection of bound of biotin-labelled rshCD5 or rshCD6 to E. coli or S. aureus (D) Detection of bound (B) and unbound (NB) individual ectodomains of CD5 (CD5.DI, CD5.DII or CD5.DIII) to C. albicans and C. neoformans.

Figure 2:
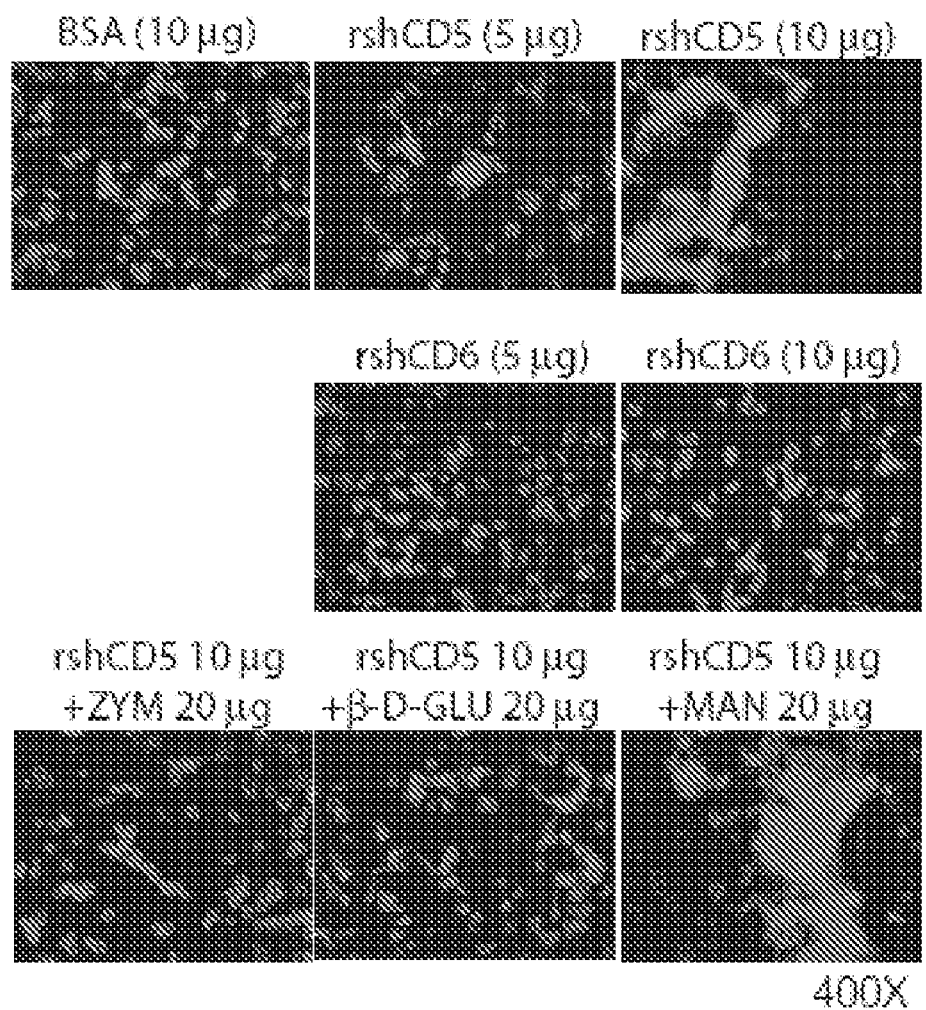

FIG. 2. Induction of fungal cell aggregation by rshCD5.

FITC-labeled C. albicans cell suspensions incubated with bovine seroalbumin (BSA), rshCD5 and rshCD6 either alone (upper and intermediate panel) or in the presence of excess amounts of zymosan or β-glucan or mannan (lower panel).

Figure 3:
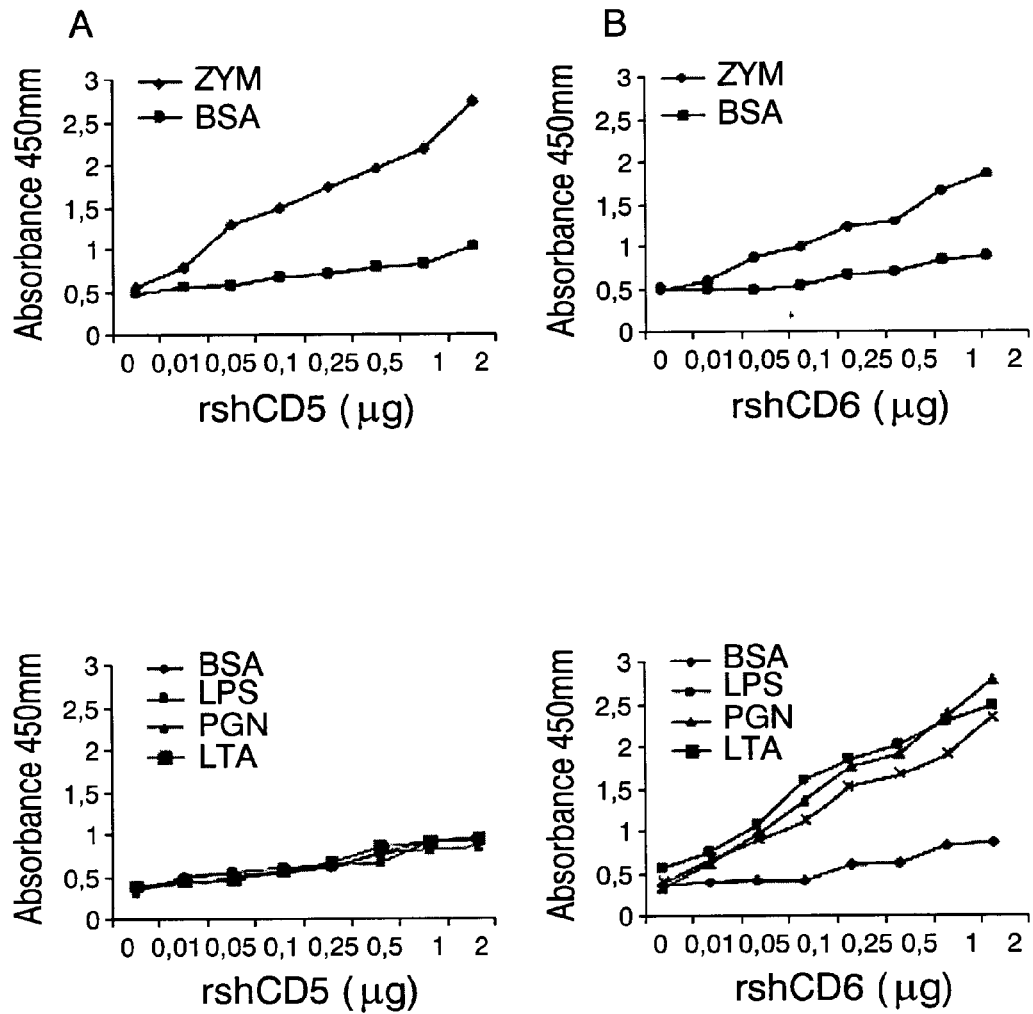

FIG. 3: Binding of rshCD5 to zymosan but not bacterial cell wall constituents.

(A) ELISA plates coated with BSA, zymosan (ZYM), LPS, PGN, or LTA incubated with increasing amounts of biotin-labeled rshCD5. (B) ELISA plates coated with BSA, ZYM, LPS, PGN, or LTA incubated with rshCD6.

Figure 4:
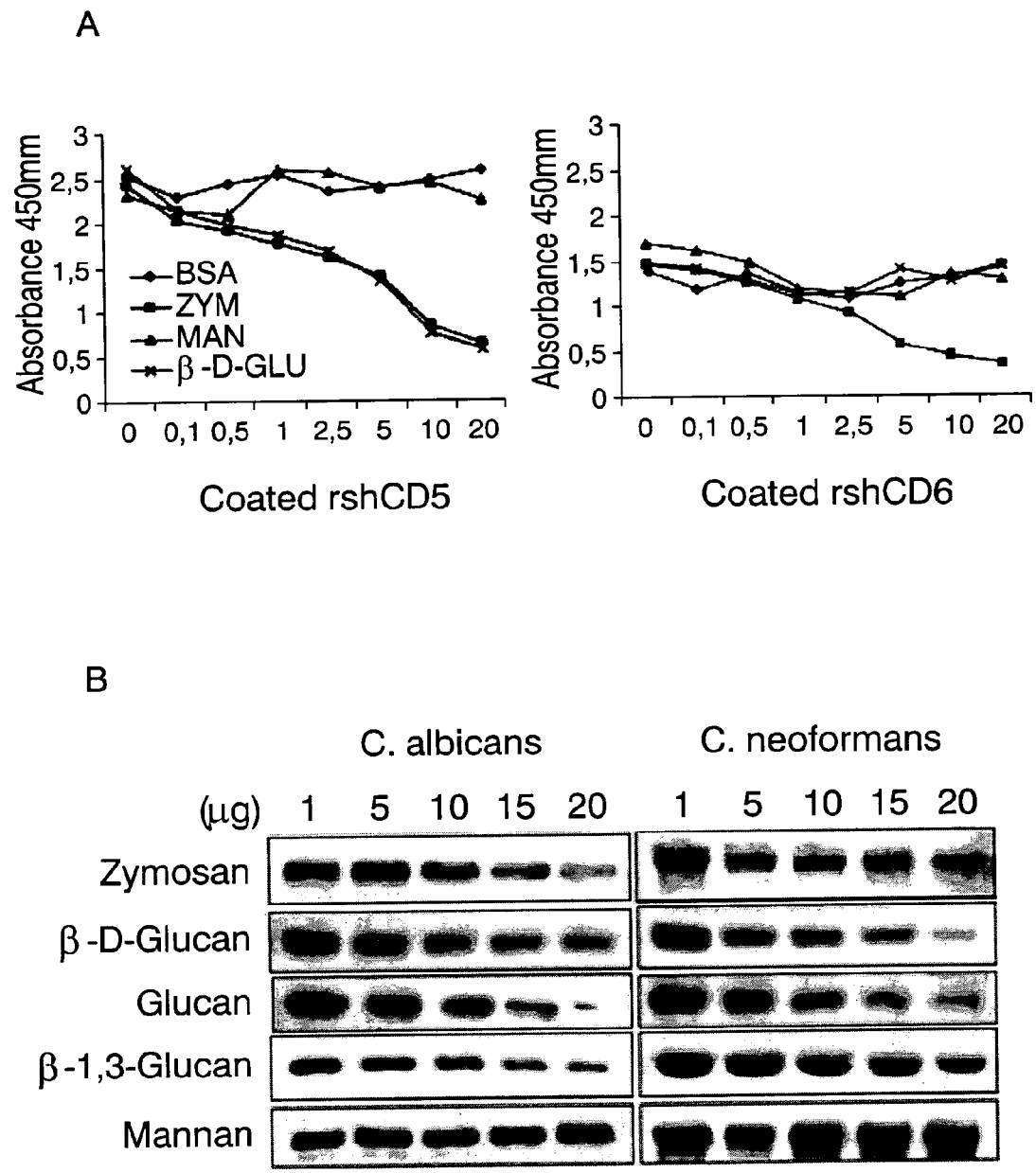

FIG. 4. Binding of rshCD5 to either zymosan or whole fungal cells is competed by β-glucans.

(A) Binding of biotin-labelled rshCD5 and rshCD6 to ELISA plates coated with zymosan competed in the presence of increasing amounts of β-D-glucans, zymosan, mannan or BSA. (B) Binding of biotin-labeled rshCD5 to C. albicans or C. neoformans cell suspensions competed in the presence of increasing amounts of zymosan, β-D-glucan, glucan, β-1,3-glucan, or mannan.

Figure 5:
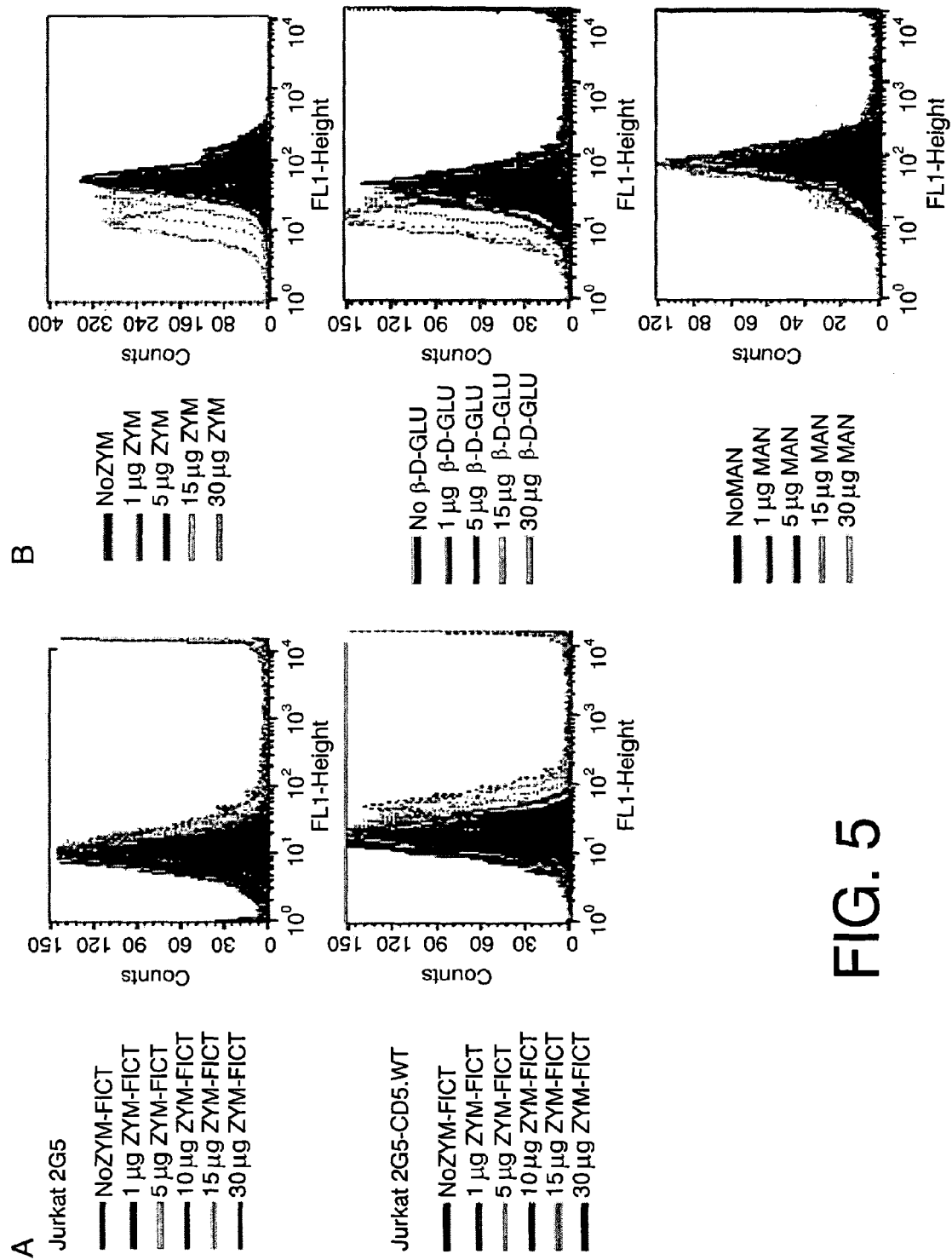

FIG. 5: FITC-labelled zymosan binds to membrane CD5.

(A) Increasing amounts of FITC-labelled zymosan incubated with CD5- and CD6-deficient 2G5 Jurkat cells either untransfected (top histogram) or transfected (bottom histogram) to express the wild-type membrane CD5 receptor (2G5-CD5.WT) (B) Jurkat 2G5 transfectants expressing the wild-type membrane CD5 receptor (2G5-CD5.WT) stained with FITC-labelled zymosan in the presence of increased amounts of zymosan (top), β-D-glucan (intermediate) and mannan (lower).

Figure 6:
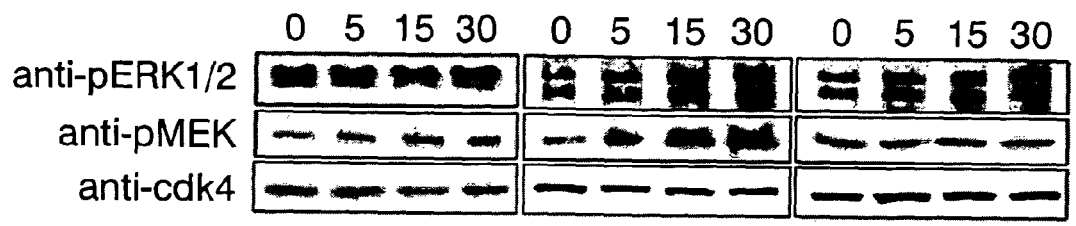
Figure 6:
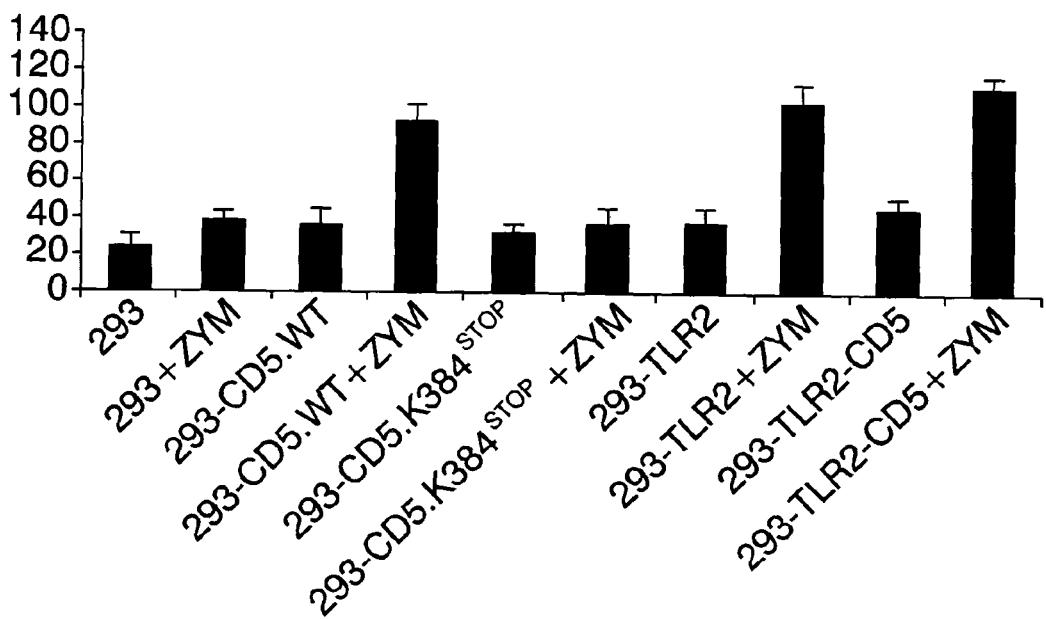
Figure 6:
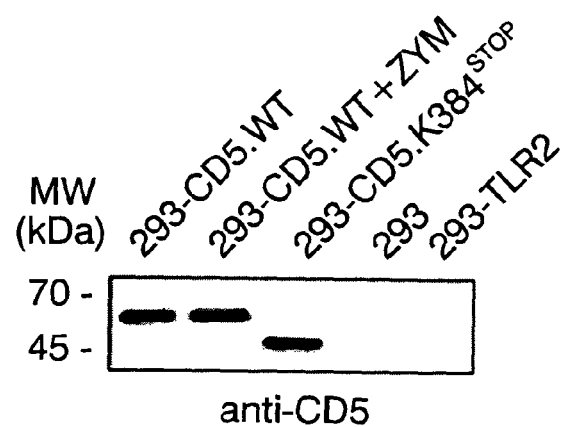

FIG. 6. Zymosan induces CD5-mediated MAPK cascade activation and cytokine release.

(A) 2G5 Jurkat cells expressing wild-type (2G5-CD5.WT) or cytoplasmic-tail truncated (2G5-CD5-K384$^{STOP}$) forms of CD5, pulsed with zymosan and analyzed by Western blot with polyclonal rabbit anti-phosphorylated ERK1/2 (pERK1/2), moclonal mouse anti-phosphorylated MEK (pMEK), and polyclonal rabbit anti-cdk4 antiserum as a loading control. (B) Zymosan-induced IL-8 release from HEK 293 cells or HEK 293-TLR2 cells transiently expressing wild-type (CD5.WT) or cytoplasmic tail-truncated (CD5.K384$^{STOP}$) membrane CD5 forms. (C) Western blot analysis of CD5 expression in cell samples from experiment shown in (B).

Figure 7:
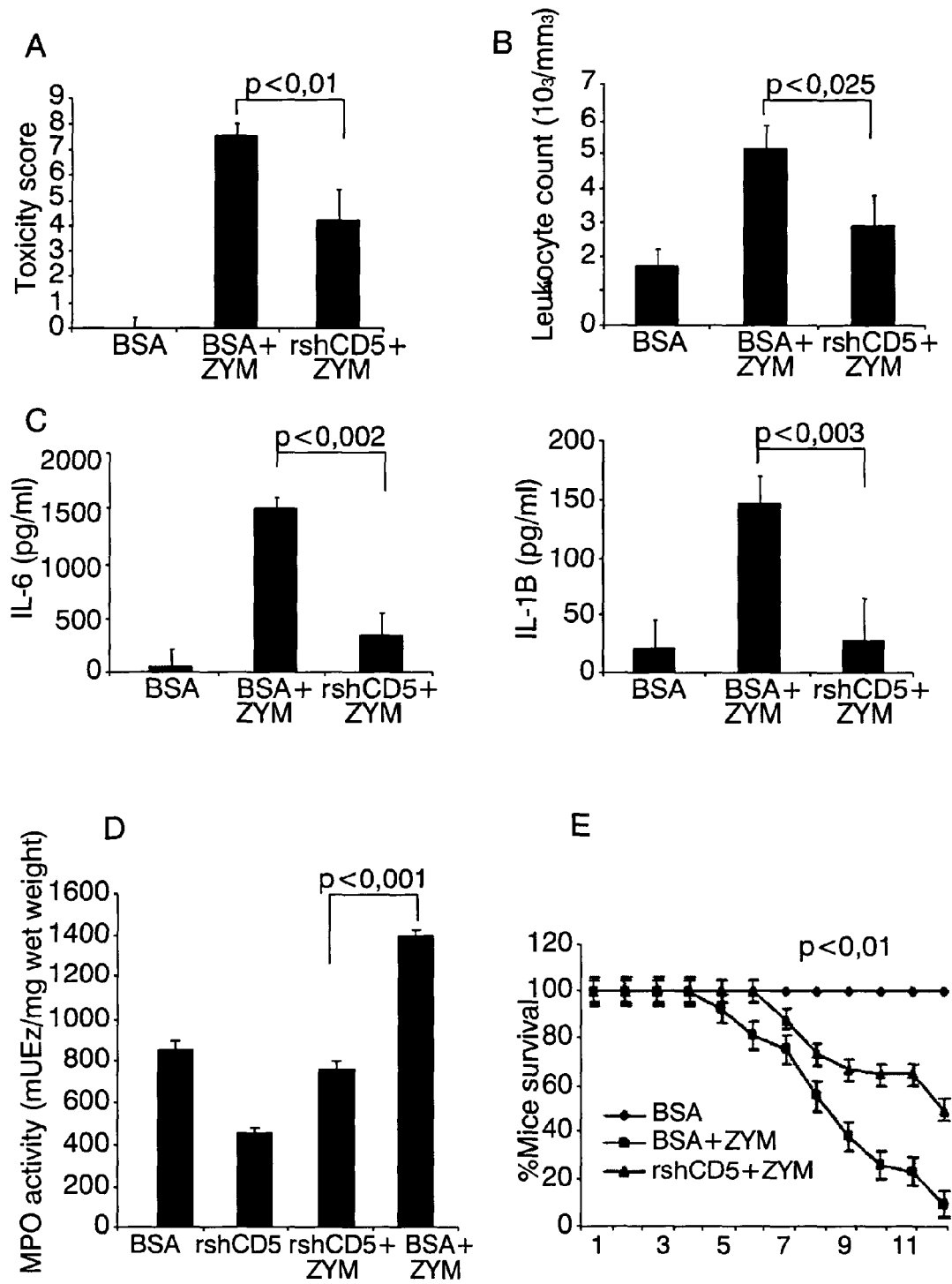

FIG. 7. Pre-treatment with rshCD5 protects from septic shock-like syndrome induced by zymosan in mice.

(A) Toxicity score of CD1 mice allocated into the groups: BSA, mice infused with BSA (25 μg; i.p.) alone; BSA+ZYM, mice pre-treated with BSA (25 μg; i.p.) before infusion with zymosan (500 mg/kg; i.p.); rshCD5+ZYM, mice pre-treated with rshCD5 (25 μg; i.p.) before infusion with zymosan (500 mg/kg; i.p.). (B) Total leukocyte count in peritoneal exudates at 18 h post-zymosan administration from the same group animals as in A. N=20 for each group. (C) IL-6 (left) and IL-1β (right) serum levels at 18 h post-zymosan administration from the same group animals as in A. N=15 for each group. (D) Myeloperoxidase (MPO) activity (mU/mg wet tissue) at 18 h post-zymosan administration in the liver from the same group animals as in A. N=3 for each group. (E) Survival curves of mice from the same groups as in A. N=25 by group.

OBJECT OF THE INVENTION

It is an object of the invention a pharmaceutical composition comprising the soluble ectodomain of the CD5 lymphocyte receptor and at least a pharmaceutical excipient.

It is also an object of the invention the use of the soluble CD5 ectodomain for fungal β-glucan binding and/or recognition.

Another object of the invention is the use of the soluble CD5 ectodomain for aggregating fungal cells and/or β-glucan-rich fungal cell wall components.

Finally, it is also an object of the invention the use of the soluble CD5 ectodomain for the manufacture of a medicament for the prevention and/or treatment of fungal infection and/or fungal sepsis and/or any inflammatory disorder related to it.

DETAILED DESCRIPTION OF THE INVENTION

The authors of the present invention have shown that the soluble CD5 ectodomain binds to and aggregates fungal cells through the recognition of conserved components on fungal cell surfaces, namely β-glucans.

Therefore, in a first aspect, the invention refers to a pharmaceutical composition comprising soluble forms of either the whole CD5 ectodomain or parts of it and at least a pharmaceutical excipient, such as Glycerol, Sacarose, etc.

An ectodomain is the part of a membrane protein that extends into the extracellular space (the space outside a cell). The extracellular region of CD5 is composed of three consecutive group B SRCR domains (CD5.D1, CD5.DII and CD5.DIII). All the three individual SRCR ectodomains of CD5 retained the ability to interact with fungal cell surfaces. Therefore, in the context of the present invention, the "soluble CD5 ectodomain" is considered to be either of CD5.DI, CD5.DII and CD5.DIII domains or combinations including any of them.

The pharmaceutical compositions of the invention may be administered by infusion or injection by systemic via, preferably intravenously or intraperitoneally. In a preferred embodiment, the soluble CD5 ectodomain pharmaceutical composition is in injectable form.

The infusion of soluble CD5 ectodomain is beneficial for the prevention and/or treatment of fungal infection and/or sepsis of fungal origin. Further, soluble CD5 ectodomain is also useful for the prevention and/or treatment of inflammatory processes triggered by fungal components, even though an active clinical infection (or sepsis) does not take place. Fungal wall components trigger inflammatory reactions, regardless of whether clinical infection proceeds or not, and, in that cases, soluble CD5 ectodomain can be also effective because it acts preventing their inflammatory effects.

Therefore, another aspect of the invention refers to the soluble CD5 ectodomain pharmaceutical composition for the prevention and/or treatment of fungal infection and/or sepsis and/or any inflammatory disorder related to it, such as SIRS or Systemic Inflammatory Response Syndrome; Aseptic serositis, etc.

The infection and/or sepsis and/or the inflammatory disorder is caused by saprophytic and non-saprophytic fungal species. In a particular embodiment, the fungal species are *Candida albicans* or *Criptococcus neoformans*.

Another aspect of the invention refers to the use of the soluble CD5 ectodomain for β-glucans binding and/or recognition.

The binding of the soluble CD5 ectodomain is dose-dependant and saturable, and is greatly facilitated by $Ca^{2+}$.

Another aspect refers to the use of the soluble CD5 ectodomain for aggregating fungal cells and/or β-glucan-rich fungal cell wall components of several fungal species (either saprophytic or pathogenic).

The fact that the soluble ectodomain of CD5 not only binds but also aggregates fungal cells is of relevance since aggregation is a common strategy used by components of the innate immune system to difficult pathogen dissemination and to facilitate pathogen clearance by phagocytes.

Another aspect of the invention refers to the use of the soluble CD5 ectodomain for the manufacture of a medicament for the prevention and/or treatment of fungal infection and/or sepsis and/or any inflammatory disorder triggered by fungal components.

The infection and/or sepsis and/or the inflammatory disorder is caused by saprophytic and non-saprophytic fungal cell species. In a particular embodiment, these fungal species are *Candida albicans* or *Criptococcus neoformans*.

The generation of recombinant soluble human of CD5 DIII ectodomains (rshCD5.DIII) has been previously described (5).

Now, the authors of the present invention have developed new primers for the generation of expression constructs for recombinant soluble human of CD5 DI and DII ectodomains (rshCD5.DI and rshCD5.DII). Oligonucleotides for the amplification of rshCD5 DI ectodomain are SEQ ID NO 1 and SEQ ID NO 2, and oligonucleotides for the amplification of rshCD5 DII are SEQ ID NO 3 and SEQ ID NO 4.

Therefore, another aspect of the invention refers to a method for obtaining a recombinant soluble human CD5 DI ectodomain (rshCD5.DI), which comprises:

a) PCR amplification of DI ectodomain using the primers of sequences SEQ ID NO 1 and SEQ ID NO 2,
b) Cloning the amplified fragment into a expression vector, and
c) Expression and Purification of the soluble human recombinant CD5 DI ectodomain.

In a preferred embodiment, the amplified fragment is cloned into appropriately digested pCEP-Pu vector (Kohfeldt et al, 1997).

In another preferred embodiment, the expression of the soluble human recombinant CD5 DI ectodomain is in HEK 293-EBNA cells.

Finally, another aspect of the invention refers to a method for obtaining a recombinant soluble CD5 DII ectodomain, which comprises:

a) PCR amplification of DII ectodomain by using the primers of sequences SEQ ID NO 3 and SEQ ID NO 4.
b) Cloning the amplified fragment into a expression vector, an
c) Expression and Purification of the recombinant CD5 DII ectodomain.

In a preferred embodiment, the amplified fragment is cloned into appropriately digested pCEP-Pu vector.

In another preferred embodiment, the expression of the soluble human recombinant CD5 DII ectodomain is in HEK 293-EBNA cells.

The following examples by way of illustration and not limitation, further define the present invention:

EXAMPLES

Example 1

The SRCR Ectodomains of Human CD5 Bind to Whole Fungal Cell Suspensions

Figure 1:
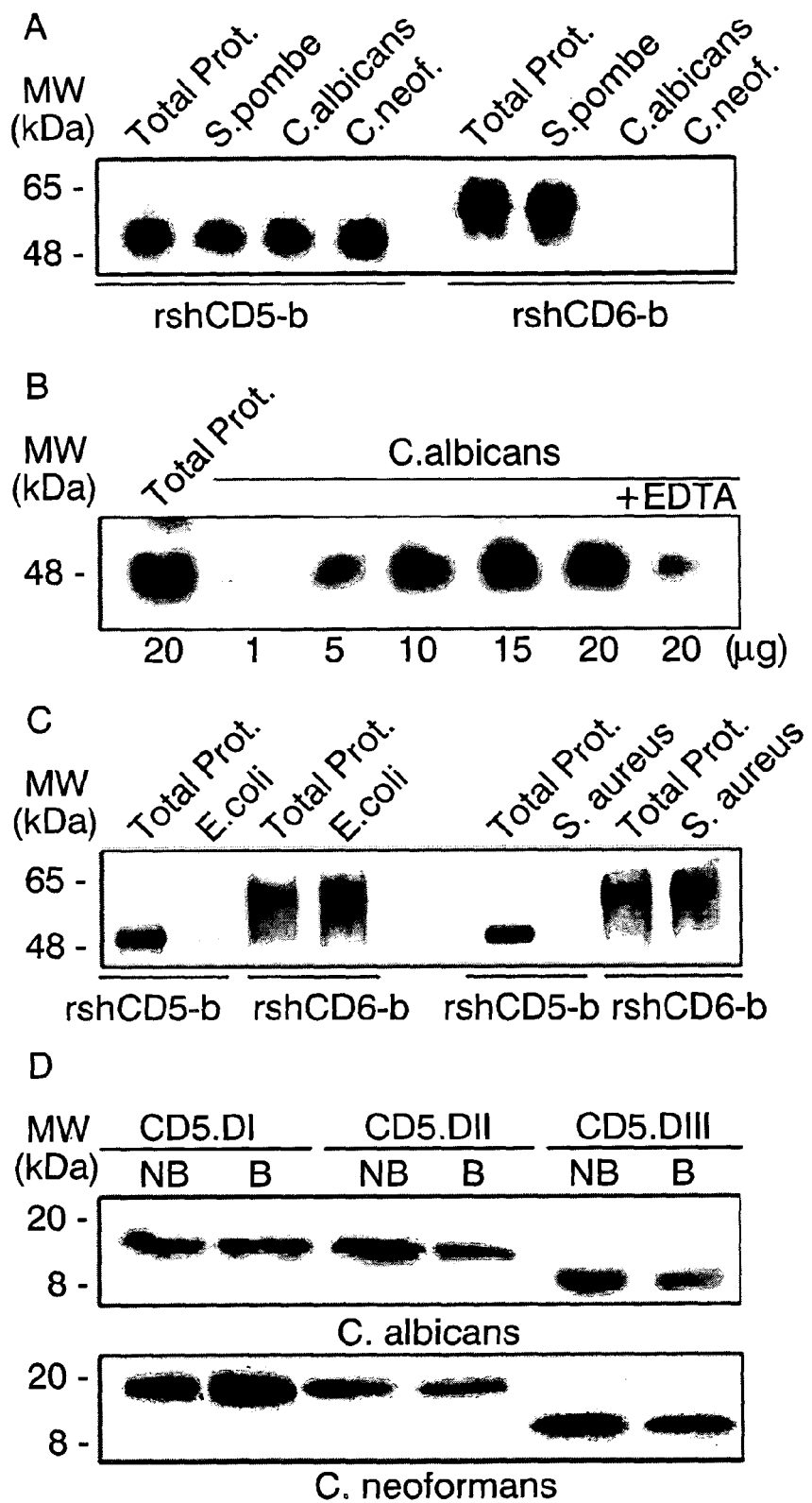
FIG. 1. Interaction of the CD5 ectodomain with whole fungal cells.

In an effort to further extend the studies on the microbial binding properties of the ectodomains of the human CD5 and CD6 lymphocyte receptors (39), the authors of the present invention performed direct protein binding assays to fungi. To this, a fix amount (15 μg) of biotin-labelled preparations of affinity-purified recombinant soluble proteins encompassing the three SRCR ectodomains of human CD5 (rshCD5) or human CD6 (rshCD6) were incubated with $10^8$ *S. pombe, C. albicans* or *C. neoformans* cells overnight at 4° C. These rshCD5 and rshCD6 proteins have been previously shown to be indistinguishable (in apparent molecular mass, antibody reactivity, and cell binding properties) from equivalent circulating forms present in normal human serum (33, 39). After extensive washing, protein binding was solubilized with Laemmli's sample buffer and run on SDS/PAGE gels and further Western blotting against horseradish peroxidase-labelled streptavidin (HRP-SAv) and further development by chemiluminescence. The results showed that rshCD5 binds to the saprophytic (*S. pombe*) and the pathogenic (*C. albicans, C. neoformans*) fungal cell species tested, while rsCD6 binds only to the saprophytic one (FIG. 1A). The binding of different amounts (from 1 to 20 μg) of biotin-labelled rshCD5 to *C. albicans* was analyzed as in FIG. 1A. The binding of 20 μg of biotin-labelled rshCD5 in presence of 5 mM EDTA is also shown. The binding of rshCD5 was shown to be dose-dependent and saturable, and was greatly facilitated by $Ca^{2+}$ since reduced binding was observed following the addition of EDTA (FIG. 1B). When the same protein preparations were tested for binding to $10^8$ gram-negative (*E. coli*) or gram-positive (*S. aureus*) bacteria, either little or no binding was observed for rshCD5 (FIG. 1C) according to previously reported data (39). This indicates that, contrary to that of CD6, the extracellular region of CD5 is well suited for recognition of fungal but not bacterial cell wall structures.

In order to identify which of the three SRCR domains (CD5.DI, CD5.DII, and CD5.DIII) of the extracellular region of CD5 was involved in fungal binding further whole fungal cell binding assays, cell culture supernatants from HEK 293-EBNA transfectants expressing individual soluble SRCR domains of rshCD5 were incubated with $10^8$ C. albicans or C. neoformans overnight at 4° C. Unbound protein (NB) was washed off and precipitated with 10% trichloroacetic acid (TCA). TCA-precipitable and cell-bound (B) proteins were electrophoresed in SDS-PAGE gels and analyzed by Western blot with a rabbit polyclonal anti-CD5 antiserum plus HRP-labelled sheep anti-rabbit antiserum, and further development by chemiluminescence. As illustrated by FIG. 1D, all the three individual SRCR ectodomains of CD5 retained the ability to interact with fungal cell surfaces. This indicates that a conserved structural motif shared by all three SRCR ectodomains of CD5 is responsible for fungal scavenging.

Example 2

Induction of Fungal Cell Aggregation by the Soluble CD5 Ectodomain

In order to investigate whether the existence of multiple binding sites on the human CD5 ectodomain would lead to fungal aggregation, FITC-labelled C. albicans cell suspensions were incubated overnight at 4° C. with 5 or 10 µg of soluble unlabelled proteins (BSA, rshCD5 and rshCD6) and then analyzed by epifluorescence microscopy. Under these conditions, rshCD5 induced dose-dependent fungal cell aggregation, while neither rsCD6 nor BSA were able to induce such a phenomenon (FIG. 2, upper and intermediate panel). The same results were also observed when C. neoformans fungal cells were assayed. Interestingly, rshCD5-induced fungal cell aggregation was significantly reduced when the assays were performed in the presence of excess amounts (20 µg) of the zymosan (from S. cerevisiae) or t-glucan (from barley), but not of mannan (from S. cerevisiae) (FIG. 2, lower panel). This showed that binding to and aggregation of fungal cells by rshCD5 is specific and it is likely mediated through recognition of specific components of the fungal cell wall such as β-glucans.

Example 3

Direct Binding of the Soluble CD5 Ectodomain to Conserved Components of Fungal but not Bacterial Cell Walls To further confirm and characterize the fungal binding capabilities of the soluble human CD5 ectodomain, its direct binding to purified fungal cell wall preparations was assessed. To this, 96-well ELISA plates coated with BSA, zymosan, LPS, PGN or LTA were incubated with increasing amounts (from 0.01 to 2 µg) of biotin-labelled rshCD5. Bound protein was detected by the addition of HRP-SAv and further developing with 3,3',5,5'-tetramethylbenzidine liquid substrate. Absorbance was read at 450 nm. In accordance with the fungal and bacterial cell binding experiments depicted in FIG. 1, biotin-labelled rshCD5 bound to zymosan-coated plates (S. cerevisiae) in a dose-dependent fashion (FIG. 3A, upper) but not to plates coated with LPS, LTA or PGN (FIG. 3A, lower). In parallel assays, biotin-labelled rshCD6 bound to plates coated with LPS, LTA or PGN in a dose-dependent manner (FIG. 3B, lower) as expected (39). Similar dose-dependence was observed for rshCD6 to zymosan-coated plates, although absorbance values were always lower than those obtained for rshCD5 (FIGS. 3B and 3A, upper). This reinforces the above mentioned statement on the suitability of the human CD5 ectodomain for scavenging of fungal but not bacterial cell wall constituents, compared to the human CD6 ectodomain.

Further competition ELISA assays were performed to determine the specificity of the fungal cell wall component responsible for the interaction with the human CD5 ectodomain. To this, a fix amount (2 µg) of biotin-labelled rshCD5 and rshCD6 was incubated with zymosan-coated ELISA plates in the presence or absence of increasing amounts (from 0.01 to 20 µg) of unlabeled competitors (β-D-glucan, zymosan, mannan or BSA). Bound protein was detected by the addition of HRP-SAv and further developing with 3,3',5,5'-tetramethylbenzidine liquid substrate. Absorbance was read at 450 nm. In accordance with fungal aggregation results shown in FIG. 2 left, β-D-glucan and zymosan but not mannan were able to compete the binding of biotin-labelled rshCD5 to zymosan in a dose-dependent manner (FIG. 4A, left). By contrast, when the same assays were performed with biotin-labelled rshCD6, only zymosan was able to compete the binding (FIG. 4A, right).

The ability of different β-glucan-containing preparations to compete the binding of the human CD5 ectodomain to fungal cell wall structures was next analyzed. To this, the binding of a fix amount of biotin-labelled rshCD5 (15 µg) to whole fungal cells was competed with increasing concentrations of β-glucan purified from barley, β-1,3-glucan purified from Euglena gracilis, and glucan from S. cerevisiae, as well as with zymosan or mannan (both from S. cerevisiae) used as positive and negative controls, respectively. After extensive washing, bound protein was solubilized and run on SDS-PAGE. Detection of biotin-labelled rshCD5 was performed by Western blot using HRP-SAv and further development by chemiluminescence. As illustrated by FIG. 4B, all glucan preparations used competed the binding of biotin-labelled rshCD5 to both C. albicans and C. neoformans cell suspensions in a dose-dependent manner. These results showed that the interaction of the human CD5 ectodomain with fungi is likely mediated through recognition β-1,3-glucan, a highly conserved and abundant constituent of fungal cell walls.

Example 4

Zymosan Binds to Membrane-Bound CD5 and Induces CD5-Mediated Activation of MAPK Cascade The authors next questioned whether the membrane-bound form of the human CD5 receptor was also able to interact with fungal cell wall constituents. To this, it was investigated the binding of increasing amounts of FITC-labelled zymosan to either untransfected or CD5-transfected 2G5 cells, a Jurkat cell derivative selected for deficient expression of both CD5 and CD6 receptors (40). Increasing amounts (from 1 to 30 µg) of FITC-labeled zymosan were incubated with 2G5 Jurkat cells either untransfected or transfected to express the wild-type membrane CD5 receptor (2G5-CD5.WT). Fluorescence intensity of stained cells was analyzed by flow cytometry. As shown in FIG. 5A, the fluorescence intensity of 2G5 cells stably expressing the wild-type membrane-bound form of CD5 (2G5-CD5.WT) was higher compared with the parental untransfected 2G5 cells. Further confirmation of the results was obtained from competition binding experiments on 2G5-

CD5.WT stable transfectants, in which a fix amount of FITC-labelled zymosan (15 μg) was competed with increasing concentrations (from 1 to 30 μg) of unlabeled zymosan (*S. cerevisiae*), β-D-glucan (barley) and mannan (*S. cerevisiae*). Fluorescence intensity of stained cells was analyzed by flow cytometry. As shown in FIG. 5B, either β-glucan or zymosan but not mannan were able to compete the binding of FITC-labelled zymosan in a dose-dependent manner. These results are confirmatory of those obtained for rshCD5 and show that CD5-expressing cells could sense the presence of conserved fungal cell wall constituents.

Further evidence on the binding of zymosan to the membrane-bound form of CD5 was obtained from activation of members of the MAPK signalling cascade in stable 2G5 transfectants expressing either wild-type (2G5-CD5.WT) or cytoplasmic tail-truncated (2G5-CD5.K384$^{stop}$) forms of CD5 (41). To this, 2×10$^6$ 2G5 cells either untransfected or transfected were pulsed for different times (from 0 to 30 min) with 40 μg/ml of zymosan at 37° C. Subsequently cell lysate samples were electrophoresed in SDS-PAGE and analyzed by Western blot with polyclonal rabbit anti-phosphorylated ERK1/2 (pERK1/2), monoclonal mouse anti-phosphorylated MEK (pMEK), and polyclonal rabbit anti-cdk4 antiserum, the latter used as a loading control. After extensive washing, membrane was developed by chemiluminescence with HRP-labelled sheep anti-rabbit or anti-mouse Ig antisera respectively. As shown in FIG. 6A, exposure to zymosan induced a time-dependent phosphorylation of both MEK and ERK1/2 in 2G5-CD5.WT cells but not in the parental untransfected 2G5 cells. Interestingly, zymosan-induced phosphorylation of both MEK and ERK1/2 was not observed in 2G5-CD5.K384$^{stop}$ transfectants (FIG. 6A, right), which express a cytoplasmic tail-truncated CD5 form devoid of the most C-terminal 88 amino acids (41). This indicates that activation of the MAPK cascade by zymosan in 2G5 cells is dependent on the expression of CD5 as well as on the integrity of its cytoplasmic domain.

Example 5

Zymosan Induces CD5-Mediated Cytokine Release

In an attempt to further explore the biological consequences of the binding of fungal cell wall constituents to membrane-bound CD5 the authors decided to analyze subsequent cytokine release phenomena. Unfortunately, stimulation of both parental and stably transfected 2G5 cells did not result in significant cytokine release at different time-points. This unresponsiveness was observed not only following exposure to high concentrations of zymosan but also to potent T-cell specific stimuli such as combinations of anti-CD3 and anti-CD28 mAbs, thus indicating the likely existence of a blockade of cytokine release in 2G5 cells.

In light of these observations the membrane-bound form of CD5 was expressed in a non-lymphoid mammalian cell system, the human embryonic kidney (HEK) 293 cells. Both the parental HEK 293 cells and a HEK 293 cell transfectant stably expressing the TLR2, a well known receptor for zymosan, were transiently transfected for expression of the wild-type (CD5.WT) and the cytoplasmic tail-truncated (CD5.K384$^{stop}$) forms of human CD5. Then, cells were subjected to zymosan exposure (20 μg/ml) for 24 h and IL-8 concentration measured in cell culture supernatants (100 μl) by ELISA. As shown in FIG. 6B, significant IL-8 release was observed for HEK 293 cells expressing CD5.WT compared to either untransfected cells or cells expressing the truncated CD5.K384$^{stop}$ molecule. Interestingly, the IL-8 levels detected for HEK 293 cells expressing CD5.WT were similar to those observed for TLR2-expressing transfectants, used as positive control. Furthermore, co-expression of CD5.WT and TLR2 did not result in either additive or synergistic effects following exposure to zymosan. Taken together, these results indicate that the membrane-bound form of CD5 may sense the presence of fungal cell wall constituents and this initiates an independent signalling cascade resulting in cytokine release.

Example 6

Infusion of the Soluble CD5 Ectodomain Protects from Zymosan-Induced Septic Shock-Like Syndrome in Mice Further in vivo validation on the binding of the CD5 ectodomain to fungal cell wall constituents was obtained from the mouse model of septic shock-like syndrome induced by zymosan (42). It was assessed whether rshCD5 would prevent systemic inflammation and multiorgan failure induced following i.p. administration of a single high dose of zymosan (500 mg/kg). Under these conditions, zymosan causes both acute peritonitis and organ injury within 18 h as well as increased mice mortality over a period of 12 days. To this purpose, CD1 mice were allocated into the following groups: BSA, mice infused with BSA (25 μg; i.p.) alone; BSA+ZYM, mice pre-treated with BSA (25 μg; i.p.) before infusion with zymosan (500 mg/kg; i.p.); rshCD5+ZYM, mice pre-treated with rshCD5 (25 μg; i.p.) before infusion with zymosan (500 mg/kg; i.p.). As shown in FIG. 7 A-E, administration of a single i.p. dose of 25 μg of rshCD5 in mice 1 h before zymosan challenge induced significant reduction on toxicity score (FIG. 7A), total leukocyte count in the peritoneal cavity (FIG. 7B), IL-6 and IL-1β blood plasma levels (FIG. 7C), and neutrophil infiltration of the liver as measured by myeloperoxidase (MPO) activity (FIG. 7D) at 18 h. In another set of experiments, mice survival was monitored and a significant increase (45% vs 15%) at the end of the observation period (12 days) was noted for animals receiving a single i.p. dose of rshCD5 before zymosan challenge compared to controls (FIG. 7E). Taken together, these results indicate that pre-treatment of mice with rshCDS prevents the harmful systemic inflammation induced by zymosan and unveils the therapeutic potential of rshCDS for fungal septic shock.

Materials and Methods

Constructions. The generation of expression constructs for soluble proteins rshCDS (43), rshCD5.DIII (5) and rshCD6 (22) has been described elsewhere. The ectodomains DI and DII of rshCD5 were PCR amplified by using the subsequent primers: DI forward (SEQ ID NO 1) and reverse (SEQ ID NO 2). DII forward (SEQ ID NO 3) and reverse (SEQ ID NO 4). The PCR was restricted with NheI and BamHI and cloned into appropriately digested pCEP-Pu vector. The resulting constructs were transfected into HEK 293-EBNA cells as previously described (44, 45). The expression constructs coding for the wild-type (pHβ-CD5.WT) and the cytoplasmic tail-truncated (pHβ-CD5.K384$^{STOP}$) membrane-bound forms of CD5 (41) were transiently transfected into HEK 293 cells by using Lipofectamine™ 2000 Reagent (Invitrogen Life Technologies, Paisley, U.K.) according to manufacturer's instructions.

Cells. The CD5- and CD6-negative 2G5 cells were obtained by cell sorting and further cloning of Jurkat cells (40) and were cultured in BioWhittaker RPMI 1640 medium (Lonza, Verviers, Belgium) supplemented with 10% FCS (Invitrogen Life Technologies), 100 U/ml penicillin G (Laboratorios ERN, Barcelona, Spain) and 50 µg/ml streptomycin (Laboratorios Normon, Madrid, Spain) at 37° C. and 5% $CO_2$. The human embryonic kidney HEK 293-EBNA cells constitutively express the Epstein-Barr viral protein EBNA-1, allowing episomal replication of the pCEP-Pu vector, were a kind gift from Dr. T. Sasaki and Dr. Timpl (Max Planck Institute for Biochemistry, Martinsried, Germany). These cells were grown in DMEM/F12 supplemented with 10% FCS, 100 U/ml penicillin G, 50 µg/ml streptomycin and 250 µg/ml geneticin (G418, Sigma, St Louis, Mo.). The HEK 293 cells and HEK 293 stably expressing TLR2 (HEK 293-TLR2) were a kind gift of Dr. Golenbock (University of Massachusetts Medical School, Worcester, Mass.). Puromycin (50 µg/mL; Sigma) was added to culture medium for selection of stable HEK 293-EBNA/pCEP-Pu and HEK 293-TLR2 transfectants.

Expression, affinity purification, and biotin-labelling of recombinant proteins. All the recombinant soluble human proteins rshCDS, rshCD6, rshCD5.DI, rshCD5.DII and rshCD5.DIII were expressed using the episomal expression system pCEP-Pu/HEK 293-EBNA. The rshCDS and rshCD6 proteins were purified from culture supernatants by affinity chromatography with specific antibodies (22, 43). The individual ectodomains of rshCDS encompassed amino acids R1-L113 (DI), A135-F271 (DII) and F271-D369 (DIII) from the mature protein, and were used as unfractionated serum-free culture supernatants. Protein biotinylation was performed with EZ-Link PEO-maleimide-activated biotin (Pierce/Perbo Science, Cheshire, U.K.) following the manufacturer's instructions.

Bacterial and fungal binding studies. The bacterial (*S. aureus* and *E. coli*) and fungal (*C. albicans* and *C. neoformans*) strains used in this study are clinical isolates characterized by the Department of Microbiology of the Hospital Clinic of Barcelona using standard biochemical procedures. The fungal strain *S. pombe* was kindly provided for the Department of Cell Biology and Pathology of the University of Barcelona. Bacteria or fungi were grown overnight in Luria Bertoni broth (LB) at 30-37° C. with aeration and then harvested by centrifugation at 3.500×g for 10 min. Bacterial or fungal pellets were resuspended in TBS (20 mM Tris-HCl, pH 7.5, 150 mM NaCl) to a final density of $10^{10}$ bacteria or $10^8$ fungi per ml. Quantification was done by plating bacteria/fungi dilutions on agar. Binding of recombinant soluble proteins (rshCD5, rshCD6) was analyzed as previously described (14).

For competition assays 15 µg of rshCD5 were pre-incubated with different concentrations of zymosan purified from *S. cerevisiae* (Sigma), β-1-3-glucan from *Euglena gracilis* (Sigma), glucan from *S. cerevisiae* (Sigma) and β-D-glucan from barley, (Sigma) or mannan from *S. cerevisiae* (Sigma), for 1 h at 4° C., before incubation with bacterial or fungal suspensions. The fungal binding studies with the rshCD5 ectodomains DI, DII and DIII, where performed by incubating $10^8$ fungi with 1 ml of respective culture supernatants overnight at 4° C. under rotation. The unbound protein was assessed by 10% TCA precipitation. These samples and the bound protein samples were solubilised with Laemmli's sample buffer, electrophoresed in SDS-PAGE and analyzed by western blot with a rabbit anti-CD5 polyclonal antiserum produced in our laboratory plus a HRP-labelled sheep anti-rabbit Ig antiserum (DAKO, Carpinteria, Calif.).

ELISA assays. 96-well microtiter plates (Nunc, Roskilde, Denmark) were coated overnight at 4° C. with 20 µg of LPS (purified from *E. coli* 055:B5, Sigma), Lipoteichoic acid (LTA; Sigma), Peptidoglycan (PGN; Sigma) or Zymosan (ZYM; Sigma) in coating buffer (100 mM $NaHCO_3$, pH 9.5). Plates were blocked for 1 h at room temperature (RT) with PBS containing 3% BSA (Sigma). Different concentrations of biotin-labeled BSA, rshCD5 or rshCD6 were then added to the wells and incubated for 2 h at RT. Bound protein was detected by the addition of 1:2000 dilution of HRP-labeled SAv (Roche Diagnostics GmbH, Mannheim, Germany) for 1 h at RT. Between each incubation step, unbound protein was washed off three times with PBS 0.01% Tween-20. The ELISA was developed by adding 3,3',5,5'-tetramethylbenzidine liquid substrate (TMB; Sigma), and the absorbance was read at 450 nm.

Competition ELISA assays were performed as above except that 2 µg of biotin-labeled rshCD5 or rshCD6 were pre-incubated with different concentrations of zymosan, β-D-glucan or mannan, for 1 h at 4° C., before its addition to zymosan-coated plates.

ELISA for IL-6 and IL-1β serum levels determination was performed according to the manufacturer's protocols (R&D Systems, Minneapolis, Minn.).

Fungal aggregation assays. Fluorescence-labeling of different fungal strains was done by incubation with 100 mM FITC for 1 h at room temperature (RT). The cells were harvested by centrifugation at 3.000×g for 5 min and after several washes in PBS to remove unbound FITC, fungi were resuspended in 300 µl PBS. Five or 10 µg rshCD5 or rshCD6 were added and incubated overnight at 4° C. under gentle orbital rotation. For competition purposes 10 µg of rshCD5 or rshCD6 were pre-incubated for 1 h at 4° C. with 20 µg of zymosan, β-D-glucan or mannan. Ten µl of the suspension were transferred onto glass slides, and visualized in a fluorescence microscope (Leica Microsystems, Mannheim, Germany). The images were analyzed with Photoshop 7.0 (Adobe Systems, San Jose, Calif.)

Flow cytometry analysis. Binding of zymosan to 2G5 or 2G5-CD5.WT cells was performed by incubating $2 \times 10^5$ cells with different amounts of FITC-labeled zymosan from *S. cerevisiae* (Sigma) in blocking buffer (PBS, 10% human AB serum, 2% FCS and 0.02% sodium azide). After 1 h incubation at 4° C., cells were washed with PBS, 2% FCS and 0.02% sodium azide and analyzed on a FACScan (Becton Dickinson, Mountain View, Calif.). The competition assays were performed by incubating 2G5-CD5.WT cells with 20 µg of FITC-labeled zymosan in the presence of different amounts (from 1 to 30 µg) of unlabeled zymosan, β-D-glucan or mannan.

IL-8 cytokine release assays. HEK 293 cells and HEK 293 stable expressing TLR2 were transfected with pHβ-CD5.WT or pHβ-CD5.H418$^{STOP}$ by using Lipofectamine™ 2000 Reagent (Invitrogen) according to manufacturer's instructions. Twenty-four hour post-transfection the media was changed to growth medium (see above). The protein expression was assessed by SDS-PAGE and western blot with a rabbit polyclonal anti-CD5 antiserum and developed by chemiluminescence with a HRP-labeled sheep anti-rabbit antiserum (DAKO). Transfected cells were pulsed with 20 µg/ml of zymosan for 24 h and supernatant samples (100 µl) were collected and assayed for IL-8 by ELISA (BD OptEIA™, Human IL-8 ELISA Set, BD Biosciencies, San Diego, Calif.) following the manufacturer's instructions.

MAP kinase assays. For stimulation purposes, $2 \times 10^7$ 2G5, 2G5-CD5.WT or 2G5-CD5.H418$^{STOP}$ cells were starved for 24 h in RPMI1640 medium without FCS. Next, cells were suspended in 300 µl of RPMI1640 medium for 10 min at 37° C. and stimulated with 40 µg/ml of zymosan during 0, 5, 15 or 30 min at 37° C. Cells were disrupted in lysis buffer (50 mM Tris-HCl, pH 7.6, 50 mM NaCl, 1 mM EDTA and 0.1% Triton X-100 containing 0.5 µg/ml aprotinin, 10 µg/ml leupeptin and 1 mM PMSF). The protein content in the cell extract was measured by the method of Bradford (Bio-Rad Laboratories, Inc. Hercules, Calif.), and 20-30 µg of protein samples were analyzed by SDS-PAGE and transferred onto nitrocellulose membranes (Millipore, Bedford, Mass.). The sheets were incubated with TBS-T (20 mM Tris-HCl, pH 7.5, 150 mM NaCl, 0.05% Tween-20) containing 5% non-fat milk powder for 1 h at RT and then probed overnight at 4° C. in shaking with rabbit polyclonal anti-pERK1/2 (sc-101760, 1:1000 dilution; Santa Cruz Biotechnology, Santa Cruz, Calif.), mouse monoclonal anti-pMEK (sc-81503, 1:1000 dilution, Santa Cruz), or rabbit polyclonal anti-cdk4 (sc-260, 1:200 dilution; Santa Cruz) antibodies. After washing three times with TBS-T, the membrane was incubated with the corresponding HRP-labeled sheep polyclonal anti-mouse or anti-rabbit Ig antisera (1:2000 dilution; DAKO) for 45 min at RT. They were washed three times with TBS-T, and once with TBS and visualized by enhanced chemiluminescence with Super Signal West Dura Extended Duration Substrate (Pierce) and exposure to X-OMAT films (Kodak, Rochester, N.Y.).

Zymosan-induced septic shock-like syndrome. Male CD1 mice weighting 20-22 g (Charles River, Milan, Italy) were injected i.p. with zymosan (500 mg/kg) in 250 µl of sterile saline solution (46). A single i.p. dose of 25 µg of either rshCD5 or BSA was given 1 h prior to the zymosan challenge. A third group of mice received the same volume of sterile saline solution with a previous administration of 25 µg of BSA. 18 h after the zymosan challenge the clinical severity of systemic toxicity was scored on a subjective scale ranging from 0 to 3 where 0=absence, 1=mild, 2=moderate, 3=serious. The ranging scale was used for each toxic sign observed in the mice (lethargy, diarrhea, ruffled fur, and conjunctivitis). Values of each toxic sign of each group were added giving a final score.

For the assessment of total leukocyte count in the peritoneum, 5 ml of PBS were injected into the abdominal cavity through an incision in the *linea alba*, and the same volume recovered after a peritoneal massage of 10 seconds. Measurements were done with an automatic cell counter (Micros 60, ABX Diagnostics, Montpellier, France). Liver samples were frozen in liquid nitrogen until used for assessment of mieloperoxidase activity (MPO) as previously described (47).

The mortality of each group was monitored during a period 12 days and expressed as percentage of survival mice. The experimental procedure was approved by the ethics committee of the University of Barcelona and performed in accordance with institutional animal care guidelines that comply with regulations in Spain (RD 1201/2005), Europe (86/609) and the National Institutes of Health's Guide for the Care and Use of Laboratory Animals.

Statistical analyses. Results are presented as mean values±SEM. Unpaired t tests were used for statistical significance determination purposes. Survival was analyzed by means of a logrank test. A p-value<0.05 was considered as statistically significant.

BIBLIOGRAPHY

1. Janeway, C. A., Jr., and R. Medzhitov. 2002. Innate immune recognition. *Annu Rev Immunol* 20:197-216.
2. Gordon, S. 2002. Pattern recognition receptors: doubling up for the innate immune response. *Cell* 111:927-930.
3. Freeman, M., J. Ashkenas, D. J. Rees, D. M. Kingsley, N. G. Copeland, N. A. Jenkins, and M. Krieger. 1990. An ancient, highly conserved family of cysteine-rich protein domains revealed by cloning type I and type II murine macrophage scavenger receptors. *Proc Natl Acad Sci USA* 87:8810-8814.
4. Sarrias, M. R., J. Gronlund, O. Padilla, J. Madsen, U. Holmskov, and F. Lozano. 2004. The Scavenger Receptor Cysteine-Rich (SRCR) domain: an ancient and highly conserved protein module of the innate immune system. *Crit. Rev Immunol* 24:1-37.
5. Rodamilans, B., I. G. Munoz, E. Bragado-Nilsson, M. R. Sarrias, O. Padilla, F. J. Blanco, F. Lozano, and G. Montoya. 2007. Crystal structure of the third extracellular domain of CD5 reveals the fold of a group B scavenger cysteine-rich receptor domain. *J Biol Chem* 282:12669-12677.
6. Liu, Y., and S. Shaw. 2001. The human genome: an immuno-centric view of evolutionary strategies. *Trends Immunol* 22:227-229.
7. Bodian, D. L., J. E. Skonier, M. A. Bowen, M. Neubauer, A. W. Siadak, A. Aruffo, and J. Bajorath. 1997. Identification of residues in CD6 which are critical for ligand binding. *Biochemistry* 36:2637-2641.
8. Skonier, J. E., D. L. Bodian, J. Emswiler, M. A. Bowen, A. Aruffo, and J. Bajorath. 1997. Mutational analysis of the CD6 ligand binding domain. *Protein Eng* 10:943-947.
9. Kristiansen, M., J. H. Graversen, C. Jacobsen, O, Sonne, H. J. Hoffman, S. K. Law, and S. K. Moestrup. 2001. Identification of the haemoglobin scavenger receptor. *Nature* 409:198-201.
10. Doi, T., K. Higashino, Y. Kurihara, Y. Wada, T. Miyazaki, H. Nakamura, S. Uesugi, T. Imanishi, Y. Kawabe, H. Itakura, and et al. 1993. Charged collagen structure mediates the recognition of negatively charged macromolecules by macrophage scavenger receptors. *J Biol Chem* 268: 2126-2133.
11. Elomaa, O., M. Sankala, T. Pikkarainen, U. Bergmann, A. Tuuttila, A. Raatikainen-Ahokas, H. Sariola, and K. Tryggvason. 1998. Structure of the human macrophage MARCO receptor and characterization of its bacteria-binding region. *J Biol Chem* 273:4530-4538.
12. Jiang, Y., P. Oliver, K. E. Davies, and N. Platt. 2006. Identification and characterization of murine SCARA5, a novel class A scavenger receptor that is expressed by populations of epithelial cells. *J Biol Chem* 281:11834-11845.
13. Peiser, L., P. J. Gough, T. Kodama, and S. Gordon. 2000. Macrophage class A scavenger receptor-mediated phagocytosis of *Escherichia coli*: role of cell heterogeneity, microbial strain, and culture conditions in vitro. *Infect Immun* 68:1953-1963.
14. Sarrias, M. R., S. Rosello, F. Sanchez-Barbero, J. M. Sierra, J. Vila, J. Yelamos, J. Vives, C. Casals, and F. Lozano. 2005. A role for human Sp alpha as a pattern recognition receptor. *J Biol Chem* 280:35391-35398.
15. Lecomte, O., J. B. Bock, B. W. Birren, D. Vollrath, and J. R. Parnes. 1996. Molecular linkage of the mouse CD5 and CD6 genes. *Immunogenetics* 44:385-390.
16. Padilla, O., J. Calvo, J. M. Vila, M. Arman, I. Gimferrer, L. Places, M. T. Arias, M. A. Pujana, J. Vives, and F. Lozano. 2000. Genomic organization of the human CD5 gene. *Immunogenetics* 51:993-1001.
17. Berland, R., and H. H. Wortis. 2002. Origins and functions of B-1 cells with notes on the role of CD5. *Annu Rev Immunol* 20:253-300.
18. Jones, N. H., M. L. Clabby, D. P. Dialynas, H. J. Huang, L. A. Herzenberg, and J. L. Strominger. 1986. Isolation of complementary DNA clones encoding the human lymphocyte glycoprotein T1/Leu-1. *Nature* 323:346-349.

19. Aruffo, A., M. B. Melnick, P. S. Linsley, and B. Seed. 1991. The lymphocyte glycoprotein CD6 contains a repeated domain structure characteristic of a new family of cell surface and secreted proteins. *J Exp Med* 174:949-952.
20. Lankester, A. C., G. M. van Schijndel, J. L. Cordell, C. J. van Noesel, and R. A. van Lier. 1994. CD5 is associated with the human B cell antigen receptor complex. *Eur J Immunol* 24:812-816.
21. Gimferrer, I., M. Farnos, M. Calvo, M. Mittelbrunn, C. Enrich, F. Sanchez-Madrid, J. Vives, and F. Lozano. 2003. The accessory molecules CD5 and CD6 associate on the membrane of lymphoid T cells. *J Biol Chem* 278:8564-8571.
22. Gimferrer, I., M. Calvo, M. Mittelbrunn, M. Farnos, M. R. Sarrias, C. Enrich, J. Vives, F. Sanchez-Madrid, and F. Lozano. 2004. Relevance of CD6-mediated interactions in T cell activation and proliferation. *J Immunol* 173:2262-2270.
23. Lozano, F., M. Simarro, J. Calvo, J. M. Vila, O. Padilla, M. A. Bowen, and K. S. Campbell. 2000. CD5 signal transduction: positive or negative modulation of antigen receptor signaling. *Crit Rev Immunol* 20:347-358.
24. Brossard, C., M. Semichon, A. Trautmann, and G. Bismuth. 2003. CD5 Inhibits Signaling at the Immunological Synapse Without Impairing Its Formation. *J Immunol* 170: 4623-4629.
25. Hassan, N. J., A. N. Barclay, and M. H. Brown. 2004. Frontline: Optimal T cell activation requires the engagement of CD6 and CD166. Eur J Immunol 34:930-940.
26. Zimmerman, A. W., B. Joosten, R. Torensma, J. R. Parnes, F. N. van Leeuwen, and C. G. Figdor. 2006. Long-term engagement of CD6 and ALCAM is essential for T cell proliferation induced by dendritic cells. *Blood* 107:3212-3120.
27. Raman, C. 2002. CD5, an important regulator of lymphocyte selection and immune tolerance. *Immunol Res* 26:255-263.
28. Ibanez, A., M. R. Sarrias, M. Farnos, I. Gimferrer, C. Serra-Pages, J. Vives, and F. Lozano. 2006. Mitogen-activated protein kinase pathway activation by the CD6 lymphocyte surface receptor. J Immunol 177:1152-1159.
29. Hassan, N. J., S. J. Simmonds, N. G. Clarkson, S. Hanrahan, M. J. Puklavec, M. Bomb, A. N. Barclay, and M. H. Brown. 2006. CD6 regulates T-cell responses through activation-dependent recruitment of the positive regulator SLP-76. *Mol Cell Biol* 26:6727-6738.
30. Castro, M. A., M. I. Oliveira, R. J. Nunes, S. Fabre, R. Barbosa, A. Peixoto, M. H. Brown, J. R. Parnes, G. Bismuth, A. Moreira, B. Rocha, and A. M. Carmo. 2007. Extracellular isoforms of CD6 generated by alternative splicing regulate targeting of CD6 to the immunological synapse. *J Immunol* 178:4351-4361.
31. Van de Velde, H., I. von Hoegen, W. Luo, J. R. Parnes, and K. Thielemans. 1991. The B-cell surface protein CD72/Lyb-2 is the ligand for CD5. *Nature* 351:662-665.
32. Biancone, L., M. A. Bowen, A. Lim, A. Aruffo, G. Andres, and I. Stamenkovic. 1996. Identification of a novel inducible cell-surface ligand of CD5 on activated lymphocytes. *J Exp Med* 184:811-819.
33. Calvo, J., L. Places, O. Padilla, J. M. Vila, J. Vives, M. A. Bowen, and F. Lozano. 1999. Interaction of recombinant and natural soluble CD5 forms with an alternative cell surface ligand. *Eur J Immunol* 29:2119-2129.
34. Pospisil, R., M. G. Fitts, and R. G. Mage. 1996. CD5 is a potential selecting ligand for B cell surface immunoglobulin framework region sequences. *J Exp Med* 184:1279-1284.
35. Haas, K. M., and D. M. Estes. 2001. The identification and characterization of a ligand for bovine CD5. *J Immunol* 166:3158-3166.
36. Hohenester, E., T. Sasaki, and R. Timpl. 1999. Crystal structure of a scavenger receptor cysteine-rich domain sheds light on an ancient superfamily. *Nat Struct Biol* 6:228-232.
37. Calvo, J., L. Places, G. Espinosa, O. Padilla, J. M. Vila, N. Villamor, M. Ingelmo, T. Gallart, J. Vives, J. Font, and F. Lozano. 1999. Identification of a natural soluble form of human CD5. *Tissue Antigens* 54:128-137.
38. Ramos-Casals, M., J. Font, M. Garcia-Carrasco, J. Calvo, L. Places, O. Padilla, R. Cervera, M. A. Bowen, F. Lozano, and M. Ingelmo. 2001. High circulating levels of soluble scavenger receptors (sCD5 and sCD6) in patients with primary Sjogren's syndrome. *Rheumatology (Oxford)* 40:1056-1059.
39. Sarrias, M. R., M. Farnos, R. Mota, F. Sanchez-Barbero, A. Ibanez, I. Gimferrer, J. Vera, R. Fenutria, C. Casals, J. Yelamos, and F. Lozano. 2007. CD6 binds to pathogen-associated molecular patterns and protects from LPS-induced septic shock. *Proc Natl Acad Sci USA* 104:11724-11729.
40. Simarro, M., C. Pelassy, J. Calvo, L. Places, C. Aussel, and F. Lozano. 1997. The cytoplasmic domain of CD5 mediates both TCR/CD3-dependent and -independent diacylglycerol production. *J Immunol* 159:4307-4315.
41. Calvo, J., J. M. Vilda, L. Places, M. Simarro, O. Padilla, D. Andreu, K. S. Campbell, C. Aussel, and F. Lozano. 1998. Human CD5 signaling and constitutive phosphorylation of C-terminal serine residues by casein kinase II. *J Immunol* 161:6022-6029.
42. Genovese, T., R. Di Paola, P. Catalano, J. H. Li, W. Xu, E. Massuda, A. P. Caputi, J. Zhang, and S. Cuzzocrea. 2004. Treatment with a novel poly(ADP-ribose) glycohydrolase inhibitor reduces development of septic shock-like syndrome induced by zymosan in mice. *Crit. Care Med* 32:1365-1374.
43. Sarrias, M. R., O. Padilla, Y. Monreal, M. Carrascal, J. Abian, J. Vives, J. Yelamos, and F. Lozano. 2004. Biochemical characterization of recombinant and circulating human Spalpha. Tissue Antigens 63:335-344.
44. Nischt, R., J. Pottgiesser, T. Krieg, U. Mayer, M. Aumailley, and R. Timpl. 1991. Recombinant expression and properties of the human calcium-binding extracellular matrix protein BM-40. Eur J Biochem 200:529-536.
45. Kohfeldt, E., P. Maurer, C. Vannahme, and R. Timpl. 1997. Properties of the extracellular calcium binding module of the proteoglycan testican. FEBS Lett 414:557-561.
46. Genovese, T., R. Di Paola, P. Catalano, J. H. Li, W. Xu, E. Massuda, A. P. Caputi, J. Zhang, and S. Cuzzocrea. 2004. Treatment with a novel poly(ADP-ribose) glycohydrolase inhibitor reduces development of septic shock-like syndrome induced by zymosan in mice. Crit Care Med 32:1365-1374.
47. Mota, R. A., D. Hernandez-Espinosa, L. Galbis-Martinez, A. Ordonez, A. Minano, P. Parrilla, V. Vicente, J. Corral, and J. Yelamos. 2008. Poly (ADP-ribose) polymerase-1 inhibition increases expression of heat shock proteins and attenuates heat stroke-induced liver injury. Crit Care Med 36:526-534.
48. Santoni G. et al: "Immune cell-mediated protection against vaginal candidiasis: evidence for a major role of vaginal CD4+ T cells and possible participation of other local lymphocyte effectors" Infect. Immun. Vol. 70(9), (2002):4791-4797
49. Levitz S. M. et al: "Phenotypic and functional characterization of human lymphocytes activated by interleukin 2 to directly inhibit growth of *Cryptococcus neoformans* in vitro" J. Clini. Invest. (1993) Viol. 91:1490-1498.

The invention claimed is:

1. A method of treatment of fungal infection and/or fungal sepsis, comprising:
   a) identifying a patient in need of treatment of fungal infection and/or fungal sepsis, and
   b) administering soluble CD5 ectodomain to the patient in need thereof.

2. The method of claim 1 where the infection and/or sepsis is caused by *Candida albicans* or *Criptococcus neoformans*.

3. The method of claim 1, comprising administering a pharmaceutical composition comprising soluble CD5 ectodomain and at least a pharmaceutical excipient to the patient in need thereof.

4. The method of claim 3, wherein the excipient is selected from the group consisting of sucrose and glycerol.

5. The method of claim 3, wherein the composition is in injectable form.

6. A method of reducing the severity of fungal infection or fungal sepsis in a patient comprising:
   a) identifying a patient in need of a reduction in the severity of fungal infection or fungal sepsis, and
   b) administering soluble CD5 ectodomain to the patient in need thereof.

7. The method of claim 6, wherein fungal septic shock is reduced.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Homo sapiens

<400> SEQUENCE: 1
ggacggctag cacggctcag ctggtatgac                                30

<210> SEQ ID NO 2
<211> LENGTH: 29
<212> TYPE: DNA
<213> ORGANISM: Homo sapiens
<220> FEATURE:
<223> OTHER INFORMATION: Antisense primer rshCD5.DI

<400> SEQUENCE: 2
gtggatccta atcctggcat gtgacaaac                                 29

<210> SEQ ID NO 3
<211> LENGTH: 29
<212> TYPE: DNA
<213> ORGANISM: Homo sapiens
<220> FEATURE:
<223> OTHER INFORMATION: Sense primer rshCD5.DII

<400> SEQUENCE: 3
ggacggctag ctgctcctcc caggctgca                                 29

<210> SEQ ID NO 4
<211> LENGTH: 28
<212> TYPE: DNA
<213> ORGANISM: Homo sapiens
<220> FEATURE:
<223> OTHER INFORMATION: Antisense primer rshCD5.DII

<400> SEQUENCE: 4
gtgatcctag aaacctgagc aaaggagg                                  28